United States Patent [19]
Offenbacher et al.

[11] Patent Number: 5,928,918
[45] Date of Patent: *Jul. 27, 1999

[54] PREPARATION OF A HYDROPHOBIC POLYMER MATRIX CONTAINING IMMOBILIZED ENZYMES

[75] Inventors: Helmut Offenbacher; Bernhard Schaffar, both of Graz; Massoud Ghahramani, Semriach, all of Austria

[73] Assignee: AVL Medical Instruments AG, Schaffhausen, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/843,295

[22] Filed: Apr. 14, 1997

Related U.S. Application Data

[63] Continuation of application No. 08/534,935, Sep. 28, 1995, abandoned.

[30] Foreign Application Priority Data

Oct. 5, 1994 [AT] Austria ..................................... 1893/94

[51] Int. Cl.⁶ ............................ C12N 11/04; C12M 1/34; C12Q 1/34; C12Q 1/26
[52] U.S. Cl. .............................. 435/182; 435/18; 435/25; 435/175; 435/180; 435/287.1; 435/817
[58] Field of Search ..................................... 435/174, 176, 435/177, 180, 182, 817, 18, 25, 175, 287.1

[56] References Cited

U.S. PATENT DOCUMENTS

Re. 29,555 2/1978 Canning .............................. 260/22 CB
3,883,612 5/1975 Pratt et al. ............................... 260/862

FOREIGN PATENT DOCUMENTS

WO89/07139 8/1989 WIPO .

*Primary Examiner*—David M. Naff
*Attorney, Agent, or Firm*—Watson Cole Grindle Watson, P.L.L.C.

[57] ABSTRACT

Biological components such as enzymes are immobilized in a three-dimensional cross-linked hydrophobic polymer. An enzyme is mixed with an aqueous solvent and a non-crosslinked prepolymer having an essentially nonpolar main chain with attached polar hydrophilic groups and cross-linking groups. The resultant mixture is exposed to cross-linking temperatures to react the prepolymer via the cross-linking groups without additional catalyst or cross-linking agents, and the aqueous solvent is evaporated to form a three-dimensional cross-linked hydrophobic polymer matrix containing the enzyme. The prepolymer can be an oil alkyl resin containing the main chain with attached polar hydrophilic groups and cross-linking groups. The oil alkyl resin is cross-linked by autoxidation, and aqueous solvent is evaporated to form the polymer matrix. A biosensor is prepared having the enzyme-containing polymer matrix on the surface of a supporting layer which contains cross-linking groups that improve adhesion between the supporting layer and the polymer matrix. Catalytic particles or charge conducting particles may be in the polymer matrix, and multiple polymer matrixes with different enzymes may be formed.

20 Claims, 7 Drawing Sheets

PREPARATION OF A HYDROPHOBIC POLYMER MATRIX CONTAINING IMMOBILIZED ENZYMES

CROSS-REFERENCE TO RELATED APPLICATION

This application is a continuation of application Ser. No. 08/534,935 filed Sep. 28, 1995 now abandoned.

BACKGROUND OF THE INVENTION

The invention relates to a method for immobilizing biological components, preferably enzymes, in a polymer matrix, and to an immobilization product prepared with this method, and to biosensors prepared with the use of this immobilisation product.

DESCRIPTION OF THE PRIOR ART

For the immobilization of enzymes and other reactive biological components and the appropriate use in sensor elements for medical diagnosis a number of methods have been developed, which are summarized below.

The following immobilization methods are known today and are employed in various technologies:

(A) Immobilization of the biological components by chemical bonding
  (1) to a substrate
  (2) by cross-linkage with bifunctional cross-linking agents
  (3) in polymer networks
(B) Adsorptive binding of the biological components to active surfaces
(C) Immobilization of the biological components by physical embedding processes
(D) Hybrid processes In the following the advantages and inherent disadvantages of different methods of immobilization by physical embedding (item C) will be discussed only, since only they are of relevance to the present invention.

With this type of immobilization biological components, such as enzymes, are incorporated in macroscopic to molecular size cavities of an embedding matrix.

The following methods are known:

(a) Insertion of an enzyme between two enzyme-impermeable membrane foils (such as cellophane).
(b) Preparation of an emulsion of enzyme solutions in a cross-linking polymer; after cross-linking the enzyme solution is present in the polymer matrix in the form of droplets.
(c) Enzyme crystal suspension in cross-linked and non-cross-linked polymers.
(d) Enzyme microdomains in an uncured polymer, prepared by dissolving enzymes in polymer water latices, the mostly high-molecular polymer being converted by the addition of plasticizer-type filming agents on drying into a largely homogeneous thermoplast film in which enzyme microdroplets are dispersed (see for instance polymer dispersion in WO 89/07139).
(e) Incorporation of the biological component by migration into a resin matrix expanded by swelling (Poly HEMA, polyacrylamide cross-linked).
(f) Incorporation of the biological component by polymer precipitation in an aqueous enzyme polymer system.
(g) Immobilization of the biological component by incorporating enzymes into a polymerization cross-linking, water-soluble hydrophilic polymer (such as UV curing polyvinyl alcohol).
(h) Encapsulation of the biological component in nanocapsules, cell ghosts, etc.

The above processes have their benefits and drawbacks, depending on the specific application and type of biological component. The following general problem areas have been identified with reference to (a) Sealing, homogeneous distribution of the enzyme in the gap, fixing to the transducer; dependence on foil characteristics.
(b, c) Deactivation of the enzymes due to cross-linking additives, such as catalysts, monomers, and others. Moreover, the polymer materials suitable for embedding are not readily permeable to hydrophilic samples.
(d) For this kind of immobilization the same disadvantages are encountered as in (b, c). Furthermore, on long-term liquid contact a moderate to strong reversion of the film-forming process will take place, i.e., the polymer film will become cloudy and permeable to the biopolymer, and subsequently revert to a latex suspension.
(e, f) Solvents enhancing swelling as a rule lead to enzyme deactivation, or rather, since such polymers must be intrinsically polar, they themselves exhibit some swelling in water, which may be harmful with respect to enzyme migration. As the polymer systems used in this instance are not cross-linked, migration even is initiated by a reorientation of the molecular chains in the course of matrix relaxation.
(g) The radical-forming agents required for the cross-linking reaction, or rather, the energy-rich radiation necessary for initiating cross-linking, will strongly impair enzyme activity. The conventional hydrophilic polymers known in this context, i.e., modified polyvinyl alcohols in most cases, are characterized by extreme swelling even after cross-linking. Furthermore, the degree of cross-linking is dependent on the water content of the enzymatic prepolymer film.
(h) Although these processes are known in the literature they can only be realized at considerable technological expense.

Biosensors with long-term stability require enzyme layers which are highly active in addition to being resistant to prolonged exposure to moisture. For these reasons the following requirements should be met with respect to the immobilization of biological components:

(1) Possibility of incorporating large amounts of a biological component into the reactive layer.
(2) No (or little) loss of activity on immobilization, i.e., avoidance of reactive cross-linking agents, radical-forming agents, heavy metal catalysts, no use of degrading monomers and solvents.
(3) Immobilization under mild conditions, i.e., temperatures as low as possible, no energy-rich radiation.
(4) Maximum analyte permeability accompanied by minimum enzyme migration.
(5) Maintaining of the optimum tertiary structure for enzyme function.
(6) Complete resistance to microbial attack.
(7) Compatibility with biological media.
(8) Minimization of adhesion problems (immobilized enzyme layer—sensitive unit), high immobilization reproducibility.

(9) Simple production technology.

(10) Possibility of modifying this production technology.

SUMMARY OF THE INVENTION

It is an object of the invention to meet the above requirements as far as possible.

In the invention this is achieved by providing that at least one biological component is mixed with a prepolymer which is water-soluble or may be emulsified in water without the use of additives; and which has a main chain in which the large majority of sequences are nonpolar and to which polar hydrophilic groups are attached either directly or in side chains, and the prepolymer mixed with the biological component react by way of cross-linking groups at temperatures ranging from room temperature to 70° C., preferably up to 40° C., to form a three-dimensional cross-linked hydrophobic polymer matrix on evaporation of the aqueous solvent, in which the biological component is embedded.

In particular, it is provided by the invention that a prepolymer of the group of polycondensation, polyaddition, and polymerization resins is used whose main chain belongs to the group of polyesters, polyamides, epoxy resins, phenolic resins, polyacrylates, and polymethacrylates, whose polar hydrophilic groups are from the group of carboxylate, amino, ammonium, hydroxyl, and alkoxyl groups, and whose cross-linking group is composed of monounsaturated to polyunsaturated fatty acid esters, β-diketo-groups, secondary amino groups, protected isocyanate groups, epoxy groups, silanol and ester groups, and further that any polar sequences of the main chain belong to the group of polyoxyalkylenes, preferably polyoxyethylene of the polymerized acrylic and methyl acrylic acids, and of the hydroxy alkylacrylates and -methacrylates.

Unlike the cross-linking hydrophilic polymers discussed under item (g), the oligomers and prepolymers of the invention (non-crosslinked) have a nonpolar, or predominantly nonpolar polymer, backbone, to which ionic (quarternary ammonium, amine or carboxylate groups) and polar (—OH, —O[—CR$_2$)n—O]m-(n=2-5, m=1-100, R=H, alkyl, acryl) and other groups are attached, either directly or on short tentacular side chains adhering to the main chain, in just such numbers as to ensure that the prepolymer remains water-soluble, water-dilutable or water-emulsifiable without the use of additives, and that it contains groups which react without the addition of catalysts and without exposure to energy-rich radiation, under mild conditions, after evaporation of the solvent, to form a slightly polar, hydrophobic, three-dimensional cross-linked polymer matrix exhibiting slight to moderate swelling in water.

Although cross-linking itself should take place without participation of the biological component, it is possible under the invention that, depending on the type of cross-linking, peripheral regions of the biological component that have no influence on its function take part in the cross-linking reaction of the preopolymers. Furthermore, salt bridges may be formed between the biopolymer and the polymer matrix carrying ionic groups, which would have a stabilizing effect on the biopolymer.

An immobilization product of the invention, which consists of biological components, preferably enzymes, that are immobilized in a polymer matrix, is thus characterized in that the basic prepolymer building the matrix is water-soluble or can be emulsified in water without the use of additives, and has a main chain in which the large majority of sequences are nonpolar, and to which polar hydrophilic groups are attached either directly or in side chains, and further that the prepolymer has cross-linking groups forming a three-dimensional network at the completion of polymerization, in which the biological component is embedded.

DESCRIPTION OF THE DRAWINGS

For better understanding the invention will be further described with reference to the accompanying drawings, in which.

DETAILED DESCRIPTION OF THE INVENTION

Figure 1:
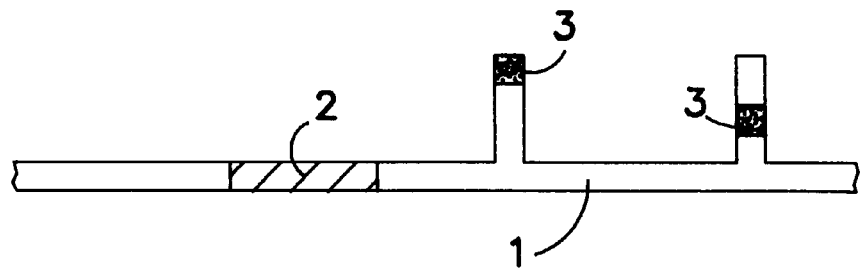
FIG. 1 is a schematical represenation of prepolymers suitable for use with the method of the invention.
Figure 1:
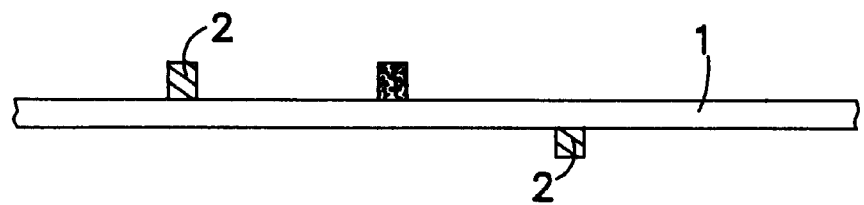
Figure 1:
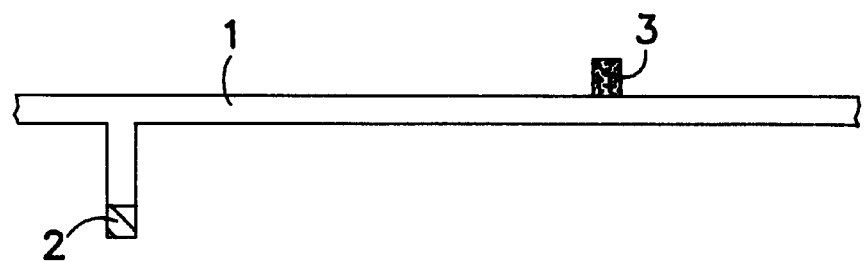
Figure 1:
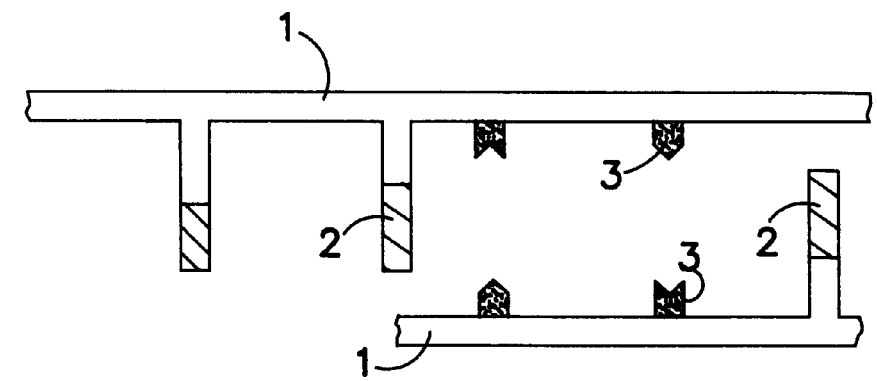
Figure 1:
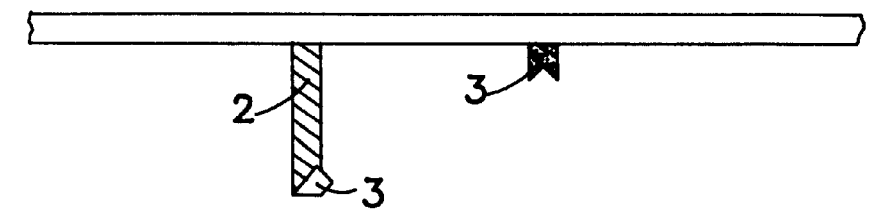

It has been found that water-soluble cross-linking synthetic coating resins with a molecular structure as shown in FIG. 1 are particularly well suited for the type of biopolymer immobilization described. In this figure the hydrophobic oligomer groups have the reference number 1, and the hydrophilic groups 2, and the reactive cross-linking groups 3. This class of substances has properties that correspond to those of the prepolymers of the invention, i.e., they are water-soluble or water-dilutable, form a film once the water has evaporated, and subsequently, after the loss of their solvent, cure in the absence of outside agents, under mild conditions, in the presence of atmospheric oxygen or at slightly elevated temperatures, to form a mechanically stable, water- resistant, intrinsically hydrophobic polymer with slight to moderate swelling.

During the process of drying and curing the polymer will retain just enough water to ensure that the biological component is incorporated in its state of optimum hydration and thus its greatest efficacy. Potential peripheral fixations do not impair the activity of this component, while being useful in further reducing the migration tendency even in the instance of wide-meshed networks. According to the invention it is an advantage if the molecule diameter of the biological component exceeds the mesh width of the three-dimensional cross-linked polymer matrix at least by a factor of 3, preferably by a factor>10, so that the biological component is retained in the polymer matrix and thus prevented from migrating.

The oligomer or prepolymer systems of the invention include the following classes of substances:

Fatty acid modified polyesters (oil alkyd resins) with a polyester backbone to which monounsaturated to polyunsaturated fatty acids are attached like tentacles, via ester formation. Features such as water-solubility or wateremulsifiability are obtained by incorporating ionic or polar groups into the main chain, or by inserting hydrophilic sequences into the main chain.

Cross-links are formed by reaction with oxygen in the air, the fatty acid side chains being intermolecularly linked via peroxide bridges. To obtain the individual structural elements the following basic materials may be used: bifunctional acids, such as phthalic anhydride, terephthalic acid, isophthalic acid, bifunctional aliphatic acids such as succinic acid, adipic and sebacic acid, and bifunctional alcohols, such as ethylene glycol, propylene glycol, neopentyl glycol, biophenol A, butylene glycol, di- and triethylene glycol, polyethylene glycol, polypropylene glycol, monoglycerides, monounsaturated to polyunsaturated fatty acids, transesterification products of linseed oils, ricinine oils, wood oils, tall oils, and other natural and synthetic fatty acid triglycerides with multifunctional alcohols, such as pentaerithritol, organic acids with a functionality of >3, fruit acids and others.

Figure 2:
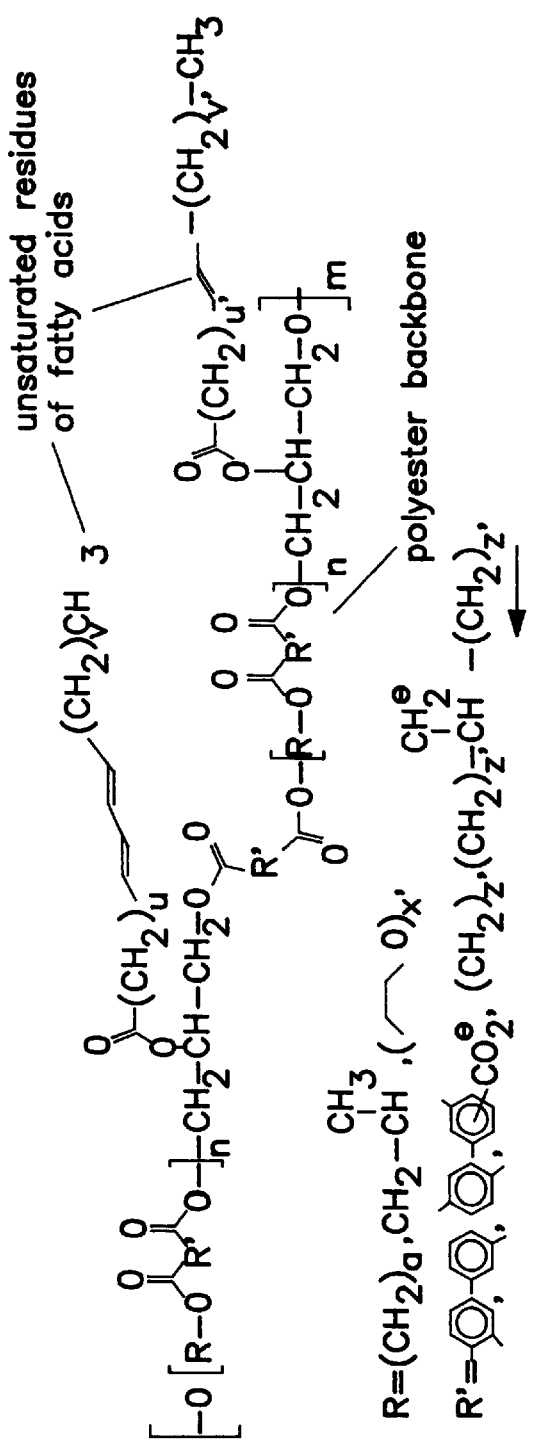
FIG. 2 shows the cross-linking reaction of suitable prepolymers curing on exposure to atmospheric oxygen, FIG. 3 the cross-linking reaction of enamine-cross-linking prepolymers, FIG. 4 a surface modification of PVC, FIG. 5 a biosensor according to the invention, built in layers, FIG. 6 a variant of FIG. 5 (glucose sensor), FIG. 7 the characteristic of a BUN (blood urea nitrogen) sensor made according to the invention, FIG. 8 gives examples of sensors a to e, FIG. 9 the characteristic of a glucose sensor made according to the invention, with electric current (nA) plotted against glucose concentration, and FIG. 10 another variant of a biosensor according to the invention.
Figure 2:
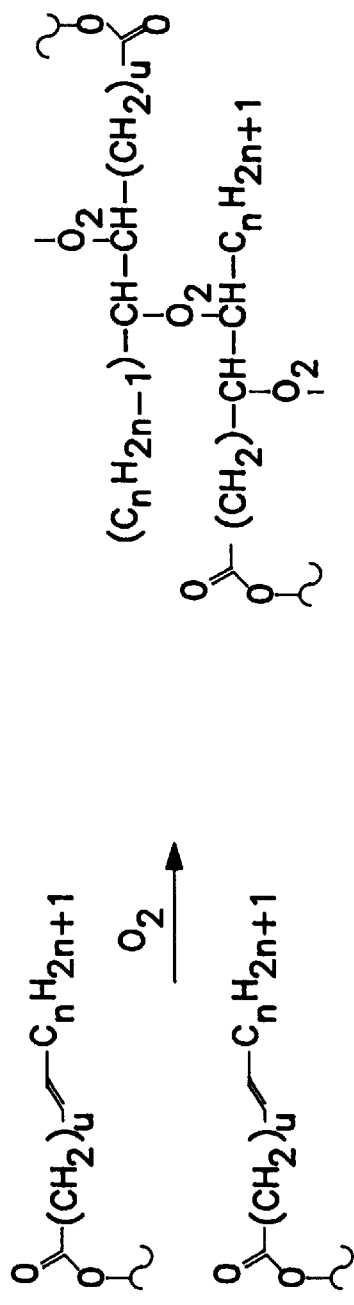

The structural principle and cross-linking reaction are presented in FIG. 2.

In the above described cross-linking by reaction with oxygen, the cross-linking temperature may be decreased to less than room temperature according to the invention, i.e., preferably to 0–5° C., if the oxygen partial pressure is raised to more than 250 millibar, preferably to more than 500 millibar. This may be of great advantage if temperature-sensitive enzymes are to be embedded.

In another variant of the invention it is provided that enamine cross-linking prepolymers be used as prepolymers, preferably polyacrylates or polymethacrylates, which are cross-linked on evaporation of the solvent, i.e., water.

Enamine cross-linking polymers essentially are polyacrylates or polymethacrylates carrying carboxyl and β-diketo groups, which are neutralized with secondary multi-functional amines, and in which the oligomer is provided in an aqueous emulsion. The oligomer-biopolymer layers prepared therefrom form a film on evaporation of the solvent, thus providing a non-porous dense matrix, which will cure at room temperature or at a slightly elevated temperature (50° C.) into a transparent polymer film exhibiting slight swelling (15% maximum weight increase after 2 hours wet storage), with the biological component embedded therein. The cross-linking reaction is presented in FIG. 3.

Preferred biological components for use in this context are one or more enzymes from the group of oxidoreductases, preferably glucose oxidase (EC 1.1.3.4), lactic oxidase (EC 1.1.3.2), or ascorbate oxidase (EC 1.10.3.3); an enzyme from the group of hydrolases, preferably urease (EC 3.5.1.5), creatinase (EC 3.5.3.3), or creatininase (EC 3.5.4.21).

As is easily seen, both the degree of cross-linking and the swelling capacity may be controlled to give good sample permeability accompanied by minimum migration of the biological component via the amount of cross-linking regions or groups and via the ratio between polar and nonpolar oligomer chain sequences, i.e., they may be influenced by mesh width and hydration capacity of the polymer chain and the cross-linking bridges.

The large family of water-dilutable and water-dispersible oligomers made hydrophobic by a mild cross-linking reaction further includes:

Silicone resin modified oil alkyds fatty acid modified polyester silicone copolymers, isocyanate resins with protected isocyanate group, epoxy resins with hydrolysis-protected epoxyfunctionality, and all hybrid resins whose features correspond to those of the oligomers capable of immobilizing biopolymers as described by the invention.

As has been mentioned before, the cross-linking reactions take place already at room temperature, after the solvent has evaporated, i.e., as the reactive groups approach each other, so that a catalyst may but need not be added. In the instance of oxidative drying of oil alkyde resins the cross-linking reaction can be accelerated in a simple way by a rise in the oxygen partial pressure and a slight increase in reaction temperature to 40–60° C. at most.

Condensation cross-linking systems, such as the enamine cross-linking β-diketo-modified poly(meth)acrylates exhibit accelerated drying at a slightly elevated temperature. Vacuum treatment and a decrease in the relative humidity have positive effects on both the rate and degree of cross-linking.

A general problem in the development of biosensors with long-term stability in aqueous systems is the adherence of the immobilization layer on the substrate, the latter being either a simple support surface or the surface of a sensitive element. A special feature of a biosensor of the invention is that the sensor has a supporting layer which is chemically modified such that it exhibits at least one group whose cross-linking capacity matches that of the prepolymer of the immobilization layer in order to improve adhesion between immobilization layer and supporting layer.

In the instance of oxidatively drying prepolymers adhesion may be improved by modifying the substrate by the immobilization of unsaturated fatty acids (double-bond fatty acids) via ester or amide.

The combination of immobilized enzyme layers and ion-sensitive electrodes is useful, for example, if by reacting a clinically relevant substrate with an enzyme an ion is produced that can be measured by a suitable ion-sensitive electrode. The sensitive element of such electrodes is typically composed of a mixture of PVC, plasticizers and suitable ionophor. If such an ion-sensitive membrane is to be made functional as regards cross-linking with the prepolymer of the enzymatic layer, the PVC component of the membrane must be modified, i.e., by using a functionalized PVC instead of the ordinary one (for instance, carboxylic polyvinyl chloride made by Aldrich, article no. 18,955-3) and modifying it in accordance with the respective requirements.

Figure 4:
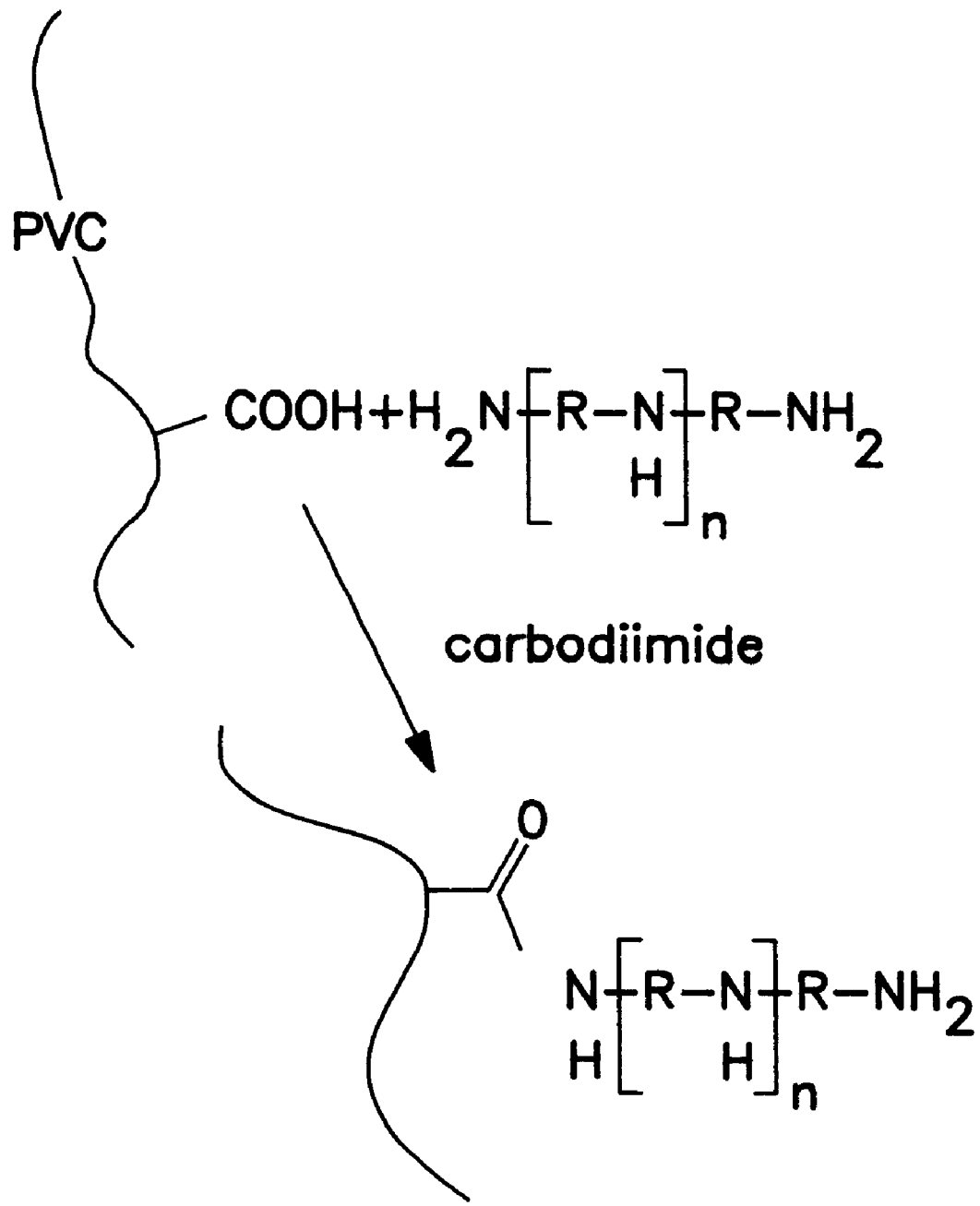

It has been found that enamine cross-linking oligomer systems will adhere well to such ion-sensitive membranes if carboxy PVC with polyamines of the $H_2N$—(R—NH—)n R—$NH_2$ class (where R=$(CH_2)_m$; n=greater 1, i.e., 1-3, m=1-10), or other classes containing at least one secondary amino group, is reacted with carbodiimide. At a low degree of PVC carboxylation such modifications will not affect electrode properties such as selectivity, membrane resistance, ionophor leaching, etc. (see FIG. 4).

In further development of the invention it is proposed that a structure of several immobilization layers be provided, which have the same matrix material but different biological components. If a largely cross-linked immobilization layer is coated with a prepolymer containing a biological component, the prepolymer layer will adhere on the lower layer to form a continuous, three-dimensional cross-linked polymer matrix during the ensuing cross-linking reaction, i.e., on evaporation of the water.

In this manner a layered structure or laminate is obtained, which is homogeneous with respect to the embedding polymer, and where each immobilization layer may contain several biological components side by side. As a consequence it is possible to have several discrete biocatalytic or reactive domains within one and the same layer. In this way catalytically active and/or charge-conducting particles such as precious metal colloids, reactive or catalytic inorganic particles, metal pigments and light-insulating pigments, as well as carbon pigments such as graphite, activated charcoal, glassy carbon, precious metal-doped carbon, etc. may be incorporated into at least one of these immobilization layers. Such measures are intended to produce layers which contain biocatalytic domains that are relevant for determining an analyte, or electrochemically active domains, or electron-conductive domains in layered form, i.e., positioned one above the other.

Figure 5:
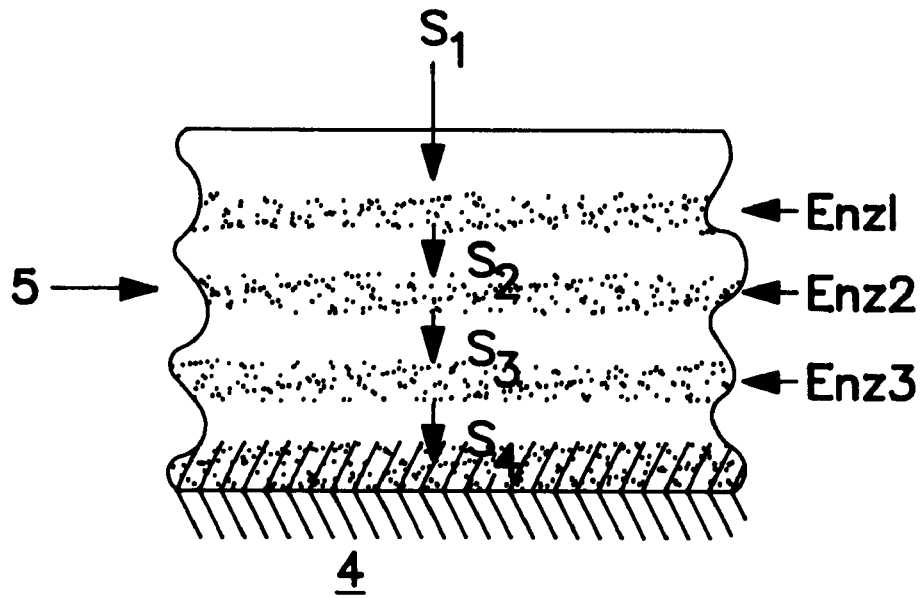

As is shown in FIG. 5, such a biosensor may be provided with several immobilization layers $S_1$ to $S_4$ on a supporting layer 4, which form a uniform polymer matrix 5 after cross-linking. The individual layers are provided with enzymes Enz1 to Enz3, the immobilization layer $S_4$ may contain catalytic and/or charge-conducting particles.

Figure 6:
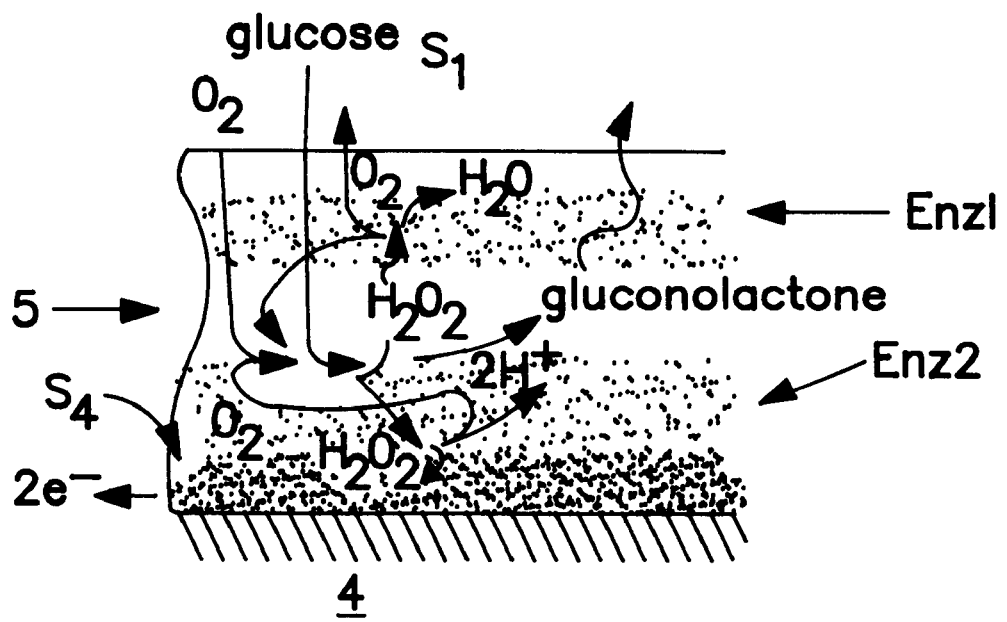

In this manner layers are obtained in which enzyme-catalyzed reaction cascades up to the sensor element can take place; in the instance of amperometric determination of substrates, such as glucose (see FIG. 6), an electrocatalytic electrode element sensitive to the product resulting from the enzymatic reaction, may be integrated into the $S_4$ layer. (Enz1=catalase, Enz2=GOD). The immobilization layer $S_4$ contains Pt and carbon particles.

An immobilization layer with a biological component additionally containing an electrocatalytic electrode element has been found to be particularly advantageous. For this purpose an aqueous oligomer including the enzyme system is filled with platinum and carbon particles such that after evaporation of the water and cross-linking of the oligomer an electrically conductive layer carrying the enzyme is formed. In this embodiment the enzyme is not adsorbed on the carbon-electrode surface, but is sealed molecularly dispersed in the spaces of the porous electrode material in the three-dimensional cross-linked polymer matrix. In this context a special embodiment is concerned with the impregnation of electrocatalytic carbon papers, where carbon containing a precious metal (e.g., glassy carbon) is coated on a mat (cf. Example 7).

Following are examples of an enzyme immobilization procedure in accordance with the invention.

EXAMPLE 1

Sensor Element for the Determination of Urea in Biological Media, such as Blood

When urea is reacted with an enzyme, ammonia is formed. As a consequence, a BUN-sensitive sensor is obtained by coating a layer of immobilized urease on a pH or $NH_4^+$ sensor. This example is designed to show the combination of immobilized urease layer and ammonium-sensitive electrode.

(a) Preparation of a PVC modified with secondary amino groups 10 g carboxy-PVC (1.8% carboxy content - Aldrich Chem. Corp.) is dissolved in 150 ml THF (Flukapuriss. pa), and 600 mg dicyclohexyl carbodiimide (Fluka) and 500 mg bishexamethylene triamine (Merck) are added. After stirring for 48 hours at room temperature the reaction solution is poured into 1000 ml acetone and 250 ml distilled water are added as a filler to the modified polymer. The mixture is filtered, rinsed with acetone, ethanol and distilled water, and suspended in ethanol for 2 hours before suction-filtering. After vacuum-drying a flaky powder of off-white color is obtained.

(b) Preparation of the ammonium-sensitive membrane 300 mg amino-PVC are dissolved with 10 mg nonactin in 3.5 g tetrahydrofuran (Fluka puriss. pa), and 660 mg bis(1-butylpentyl) adipate are added.

This membrane liquid may be introduced into the membrane window of an electrode housing (see DE 2,854,444 C2), for example, or it may be contacted with a plane, electrically conductive surface.

(c) Immobilization of the enzyme 0.5 ml of an aqueous ketimine cross-linking polyacrylate emulsion (resin content=40%) are added to 1 ml physiological phosphate buffer (pH 7.4), and then mixed with 100 mg urease (from the Madagascar bean—124 units/mg; Fluka). This mixture has good storage stability and may be stored for several weeks at 0° to +4° C. The mixture is applied dropwise on the ammonium-sensitive membrane by means of a dispenser, and held at room temperature for 1 week, or at 35° to 40° C. for 2 days.

Figure 7:
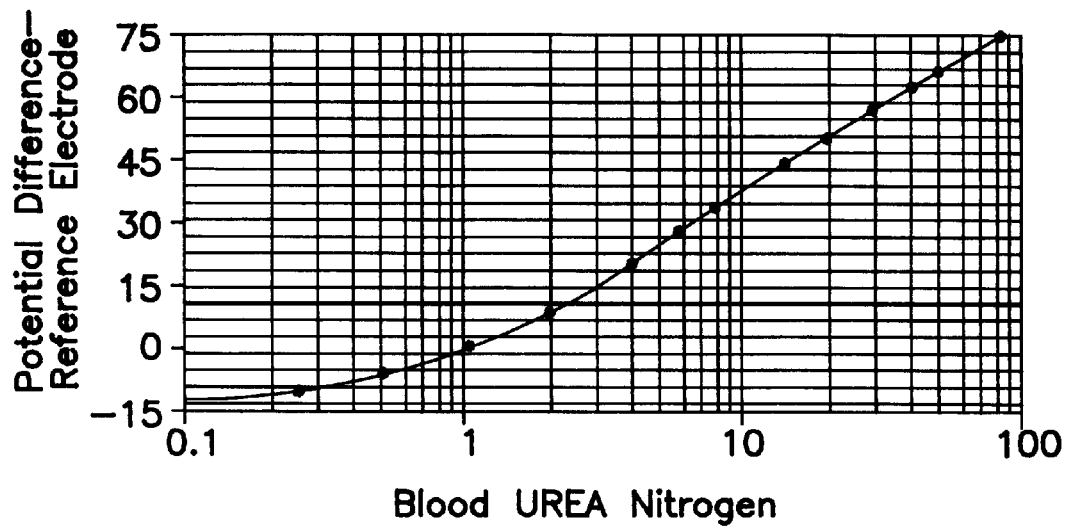

The enzyme activity test shows that an activity loss of only 10–15% is observed during cross-linking; no further activity losses were observed during subsequent wet storage in a physiological buffer system. Compared to ammonium-sensitive membranes with unmodified PVC as membrane polymer, the combination of electrode membrane and immobilization layer exhibits excellent adhesion even during wet storage in the buffer medium; the immobilization layer cannot be removed from the ammonium-sensitive membrane without destroying the latter. Water absorption by swelling of the immobilizing layer is moderate, i.e., 14% after several hours exposure to the physiological buffer system. This fact will ensure good ammonium permeability; the stability of the sensor indicates genuine enzyme immobilization. FIG. 7 gives a characteristic of a BUN (blood urea nitrogen) electrode according to the invention, BUN concentration being plotted against potential difference.

EXAMPLES 2 to 6

Sensor Element for the Determination of Glucose in Biological Media

The reaction of glucose with glucose oxidase in the absence of mediators gives rise to gluconolactone as well as hydrogen peroxide, whis is formed amperometrically and may be anodized to give oxygen. The electric current flowing during this process is a measure for the glucose content of the sample. Following are examples of sensor elements comprising several immobilization layers as described by the invention.

Preparation of the basic components (a) Preparation of linseed oil fatty acid amidohexylamine 0.2 mole linseed oil fatty acid (technical grade) are reacted at room temperature with 0.2 mole 1,6-diaminohexane (pa Merck) and 0.2 mole dicyclohexyl carbodiimide (Fluka) in 1 l ethyl acetate in an inert gas atmosphere. At completion of the reaction the resulting dicyclohexyl urea is filtered off and the organic phase is washed several times with diluted potassium chloride solution. After drying with $Na_2SO_4$ the product is concentrated by evaporation in an inert gas atmosphere until an amber-colored oil remains. The reaction product is stored over calcium oxide in an argon atmosphere.

(b) Preparation of the substrate

Small plates of polymethyl acrylate on which a conducting strip of gold has been sputtered, are surface-hydrolized with 35 percent by volume sulphuric acid, introduced into a solvent solution causing only moderate swelling of the plate, and treated with linseed oil fatty acid amidohexylamine and dicyclohexyl carbodiimide (Fluka) for 24 hours at room temperature in an inert gas atmosphere. The plates are washed with benzine and processed immediately.

(c) 1 g polyester modified with unsaturated fatty acids (oil alkyd resin made by Vianova, 40% in water) is mixed with 0.5 g platinum 10% on activated charcoal (Fluka) and 0.5 g graphite (Merck). Water is added until a vibration-millable paste is obtained. The compound can be stored at room temperature in an inert gas atmosphere.

(d) 1 g of the paste (c) is mixed with 0.05 g glucose oxidase (EC 1.1.3.4-15,000–25,000 units/g) and is stored at room temperature in an inert gas atmosphere.

(e) 1 g oil alkyd resin (40% in water) is mixed with 0.05 to 0.1 g GOD (EC 1.1.3.4-15,000–25,000 units/g); the resulting resin enzyme solution is stored at room temperature in an inert gas atmosphere.

(f) 1 g oil alkyd resin (40% in water) is mixed with 0.05 g catalase (EC 1.11.1.6-5,000 units/g); the resulting resin enzyme solution is kept refrigerated in an inert gas atmosphere.

(g) 0.5 g potassium hexachloroplatinate(IV) is dissolved in approx. 10 ml water and reduced to a platinum colloid suspension of brown color with the use of a suitable reducing agent. After thorough dialysis the colloidal suspension is mixed with the oil alkyd resin at a 1:2 ratio, and is stored at room temperature in an inert gas atmosphere.

Sensors

EXAMPLE 2

Figure 8A:
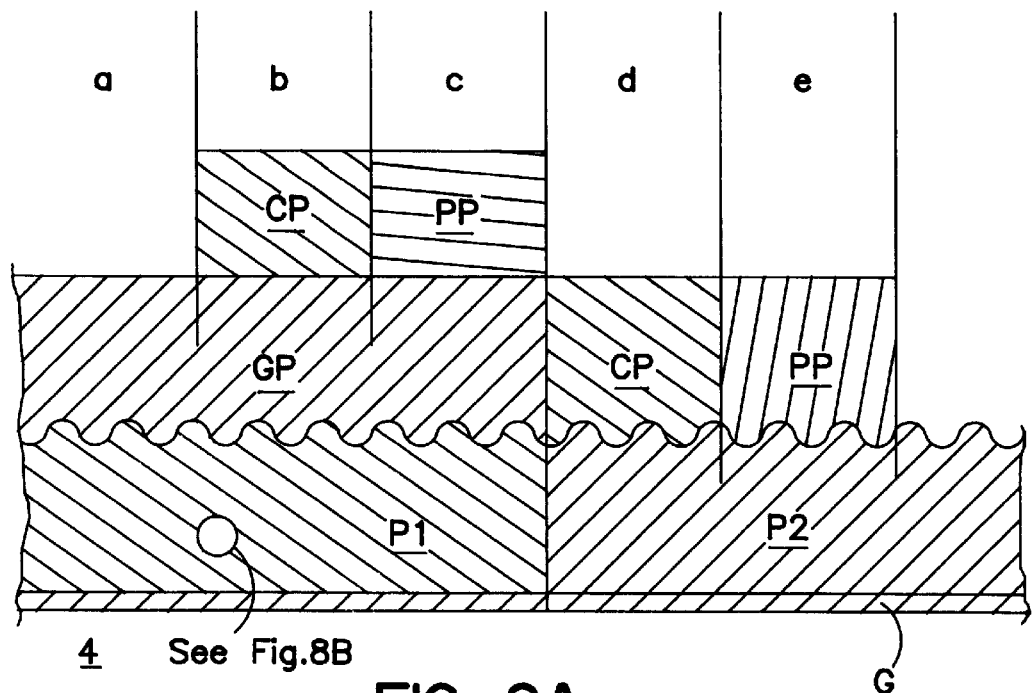

On the sensor substrate 4, i.e., the small plate provided with a conducting strip G made of gold, which is prepared as described under item (b), the paste formulation P1 described in (c) is applied using a 200–400 $\mu$m spacer, such that the layer is in contact with the gold strip G. After a drying phase of several hours at room temperature the GOD prepolymer mixture GP (item e) is applied to a thickness of 30–100 micrometers (wet film), as shown in FIG. 8a. The enlarged detailed view of layer P1 shows Pt-carbon particles 10, graphite particles 10', and the cross-linked polymer 12.

EXAMPLE 3

Figure 8B:
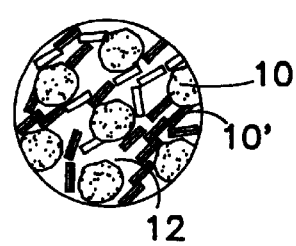

Same procedure as in Example 2; after surface drying of the GOD prepolymer layer GP, 30–100 micrometers (wet film) of the catalase prepolymer mixture CP (item f) are applied (FIG. 8b).

EXAMPLE 4

Same procedure as in Example 3; instead of the catalase prepolymer mixture the platinum colloid prepolymer mixture PP (item g) is applied (FIG. 8c).

EXAMPLES 5 and 6

The paste P2 (item d) is applied on the substrate 4 in the same way as paste P1 in Examples 2–4 and coated after an initial drying phase with formulations CP and PP, respectively, as in Examples 3 and 4 (FIGS. 8d and 8e).

All sensor variants are subjected to oxidative drying for a period of several hours to several days in an $O_2$-enriched atmosphere or in the presence of atmospheric oxygen, and are stored in a physiological buffer when the cross-linking is complete. The addition of a coat of catalase or platinum metal colloid will help prolong the linear region, and will prevent $H_2O_2$ from diffusing into the sample space—which is a requirement of in vivo measurements.

Figure 9:
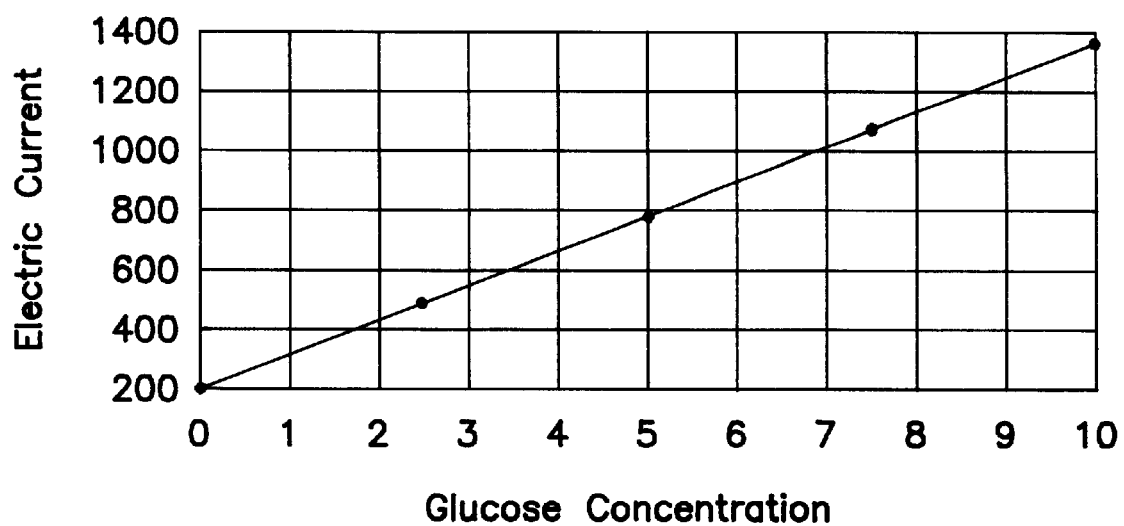

FIG. 9 presents a diagram where electric current is plotted against glucose concentration in a physiological buffer.

EXAMPLE 7

Figure 10A:
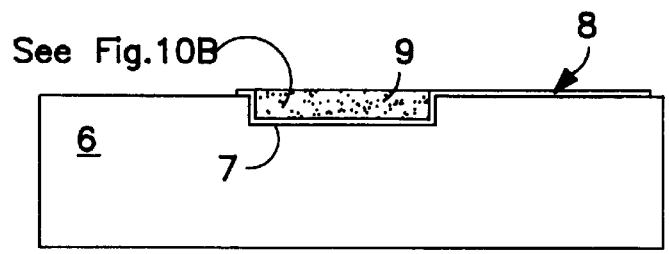
Figure 10B:
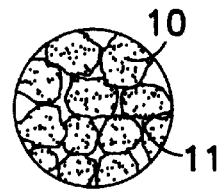
Figure 1:
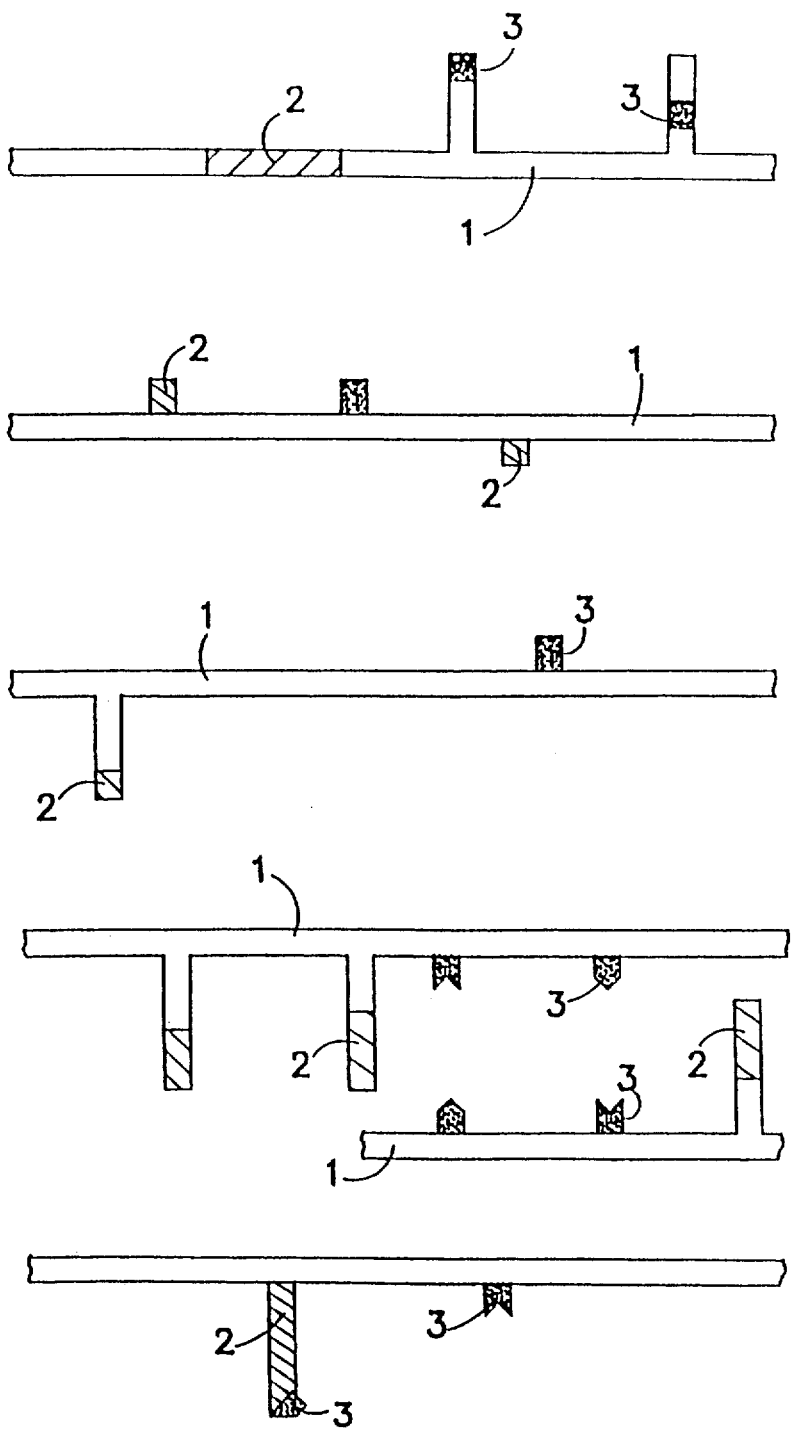
Figure 2:
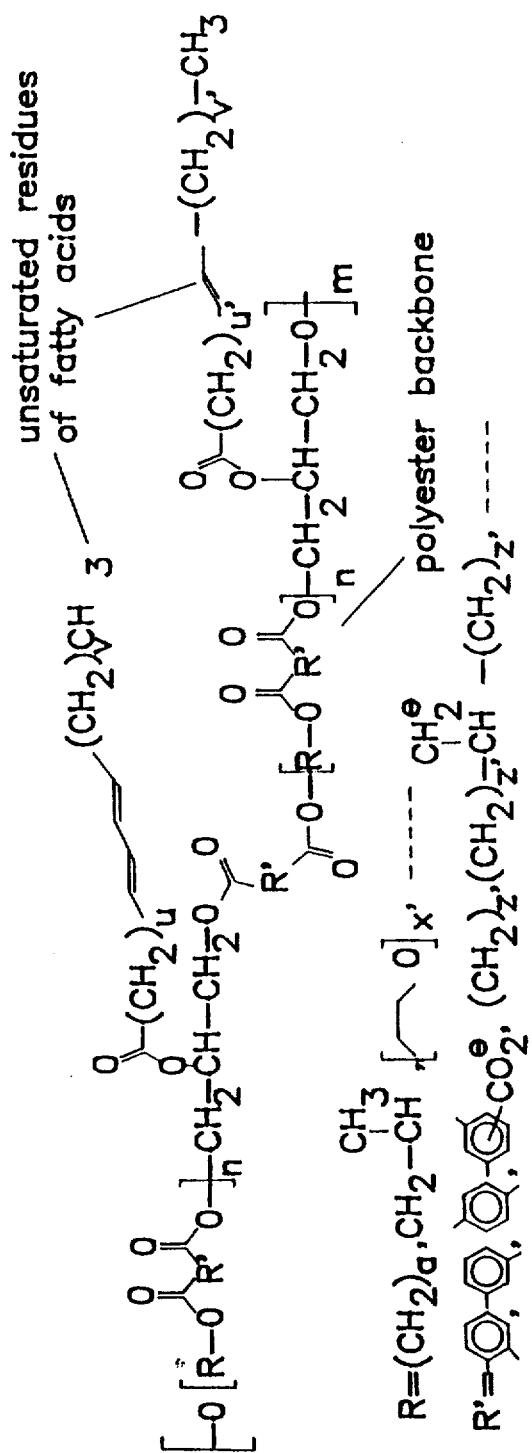
Figure 2:
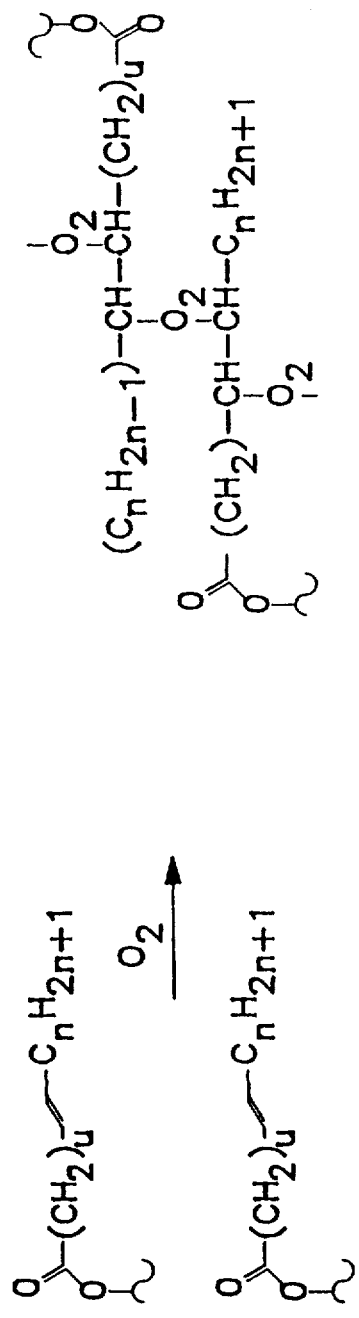
Figure 3:
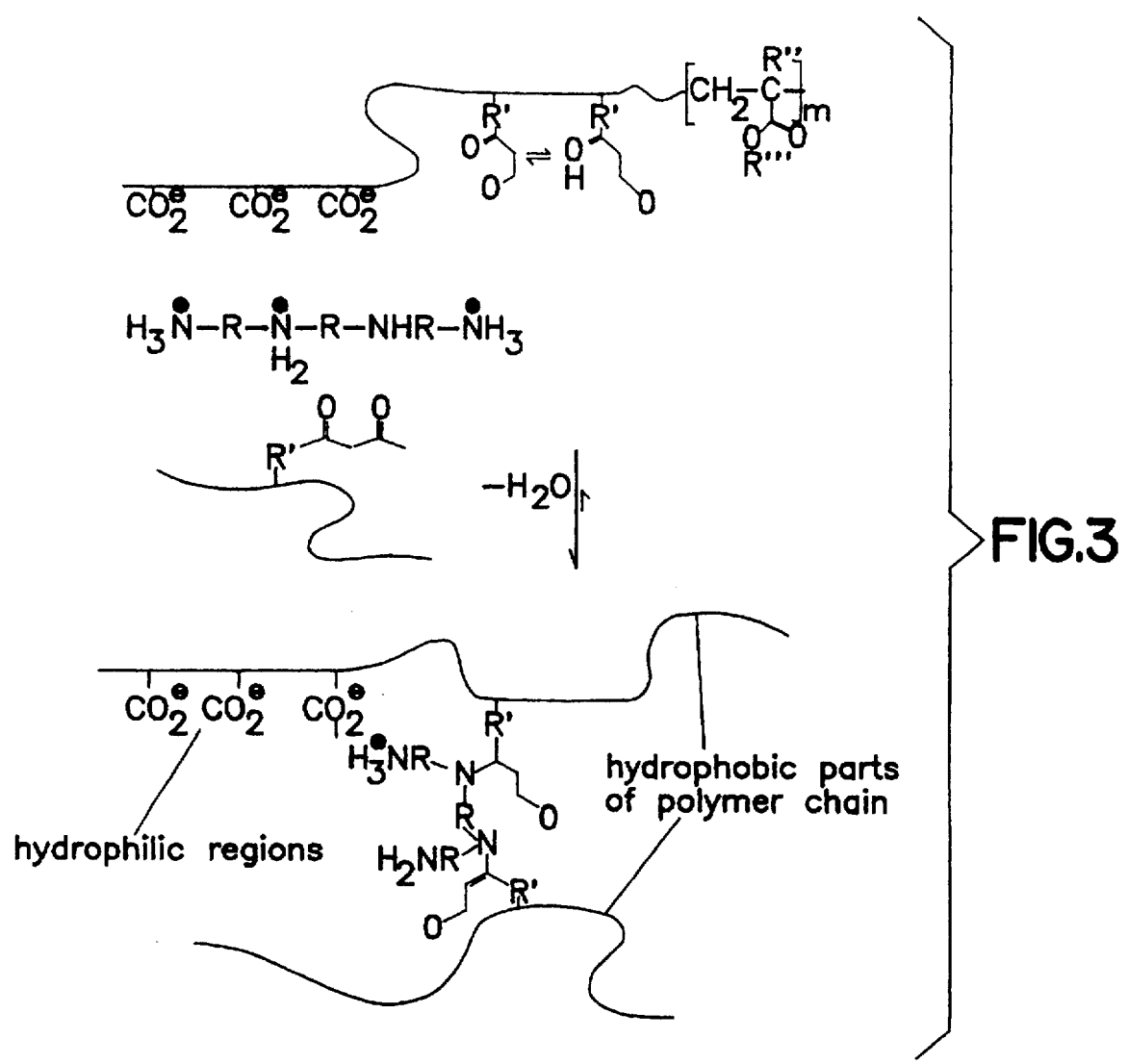

As is shown in FIG. 10, a plastic substrate 6 with a pot-shaped recess 7 is sputtered with gold such that the surface of the recessed area forms an electrically conductive unit with the contact site 8 on the sensor support. Into this recess 7 a small disk 9 is inserted, which consists of Pt-carbon supported on a mat. 100 mg lactic oxidase of pediococcus species (L 0638 Sigma-30 units/mg) are dissolved in 1 ml physiological phosphate buffer and mixed with 0.5 ml enamine cross-linking polyacrylate prepolymer (40% in water).

The inserted Pt-carbon electrode is impregnated with the enzyme/prepolymer solution, dried at room temperature and left to cure. In the enlarged detailed view of FIG. 10 the microporous Pt-carbon particles have the reference number 10, the enzyme polymer is 11.

The resulting sensor element (FIG. 10) exhibits linearity of current flow up to a lactate concentration of 15 mmole/l; its useful life is increased by a factor>5 over a sensor element in which the lactic oxidase is adsorption-bound to an identical Pt-carbon electrode material.

We claim:

1. Method for immobilizing an enzyme in a polymer matrix, comprising the steps of:
   a) mixing at least one enzyme with a non-crosslinked prepolymer and an aqueous solvent to form a mixture, said prepolymer consisting of:
      a main chain essentially nonpolar and selected from the group consisting of polyesters, polyamides, epoxy resins, polyacrylates, and polymethacrylates,
      polar hydrophilic groups attached to said main chain and selected from the group consisting of carboxylate, amino, ammonium, hydroxyl, and alkoxyl groups, and
      cross-linking groups selected from the group consisting of $\beta$-diketo- groups, secondary amino groups, protected isocyanate groups, epoxy groups, and ester groups,
   b) exposing said mixture of step a) to cross-linking temperatures ranging from room temperature up to 40° C. so that said prepolymer reacts via said cross-linking groups without additional catalysts or cross-linking agents, and
   c) evaporating said aqueous solvent to form a three-dimensional cross-linked hydrophobic polymer matrix having said enzyme embedded therein.

2. Method according to claim 1, wherein said enzyme is an oxidoreductase.

3. Method according to claim 2, wherein said enzyme is selected from the group consisting of glucose oxidase, lactate oxidase, and ascorbate oxidase.

4. Method according to claim 1, wherein said enzyme is a hydrolase.

5. Method according to claim 4, wherein said enzyme is selected from the group consisting of urease, creatinase, and creatininase.

6. Method according to claim 1, wherein said main chain comprises polar sequences selected from the group consisting of polyoxyalkylenes, hydroxy alkylacrylates and hydroxy methacrylates.

7. Method according to claim 1, wherein peripheral regions of said enzyme having no influence on the function of said enzyme participate in the reaction of step b).

8. Method according to claim 1, wherein said enzyme has a molecular diameter which exceeds a mesh width of said three-dimensional cross-linked polymer matrix at least by a factor of 3 so that said enzyme is retained in said polymer matrix and thus is prevented from migrating.

9. Immobilization product consisting of a polymer matrix having immobilized at least one enzyme and made by the method according to claim 1.

10. A bioseneor comprising a supporting layer and a layer of an immobilization product according to claim 9, on a surface of said supporting layer, said surface including at least one group having a cross-linking capacity which matches with the cross-linking capacity of said prepolymer of said immobilization product in order to improve adhesion between said immobilization product and said supporting layer.

11. A biosensor according to claim 10, comprising a plurality of immobilization products on said supporting layer which each have the same matrix material but different enzymes.

12. A biosensor according to claim 11, wherein each of said immobilization products contain a multi-enzyme system.

13. Biosensor according to claim 10, wherein said layer of immobilization product contains catalytic particles.

14. Biosensor according to claim 13, wherein said catalytic particles are precious metal colloids or precious metal pigments.

15. Biosensor according to claim 13, wherein said catalytic particles are manganese oxide particles.

16. Biosensor according to claim 10, wherein said layer of immobilization product contains charge-conducting particles.

17. Biosensor according to claim 16, wherein said charge-conducting particles are selected from the group consisting of graphite, glassy carbon, and activated charcoal.

18. Method for immobilizing an enzyme in a polymer matrix, comprising the steps of:
a) mixing at leapt one enzyme with a non-crosslinked prepolymer and an aqueous solvent to form a mixture, said prepolymer consisting of:
   a main chain essentially nonpolar and selected from the group consisting of polyesters, polyamides, epoxy resins, polyacrylates, and polymethacrylates,
   polar hydrophilic groups attached to said main chain and selected from the group consisting of carboxylate, amino, ammonium, hydroxyl, and alkoxyl groups, and
   cross-linking groups selected from the group consisting of $\beta$-diketo-groups, secondary amino groups, protected isocyanate groups, epoxy groups, and ester groups,
b) exposing said mixture of step a) to cross-linking temperatures ranging from room temperature up to 40° C. so that said propolymer reacts via said cross-linking groups as well as with amino groups of said enzyme without additional catalysts or cross-linking agents, and
c) evaporating said aqueous solvent to form a three-dimensional cross-linked hydrophobic polymer matrix having said enzyme embedded therein.

19. Method for immobilizing an enzyme in a polymer matrix, comprising the steps of:
a) mixing at least one enzyme with a non-crosslinked prepolymer and an aqueous solvent to form a mixture, said prepolymer being an oil alkyd resin consisting of:
   an essentially nonpolar main chain consisting polyesters,
   polar hydrophilic groups attached to said main chain, selected from the group consisting of carboxylate and alkoxyl groups, and
   cross-linking groups selected from mono-unsaturated to polyunsaturated fatty acid esters,
b) exposing said mixture of step a) to atmospheric oxygen, where said oil alkyd resin is cross-linked by reaction with atmospheric oxygen by autoxidation, and
c) evaporating said aqueous solvent to form a three-dimensional cross-linking hydrophobic polymer matrix having said enzyme embedded therein.

20. Method according to claim 19, wherein said mixture in step b) is subjected to a temperature between 0 and 5° C. and an oxygen partial pressure of more than 250 millibar.

* * * * *

UNITED STATES PATENT AND TRADEMARK OFFICE
CERTIFICATE OF CORRECTION

PATENT NO. : 5,928,918

DATED : July 27, 1999

INVENTOR(S) : Offenbacher et al.

Page 1 of 4

Figure 3:
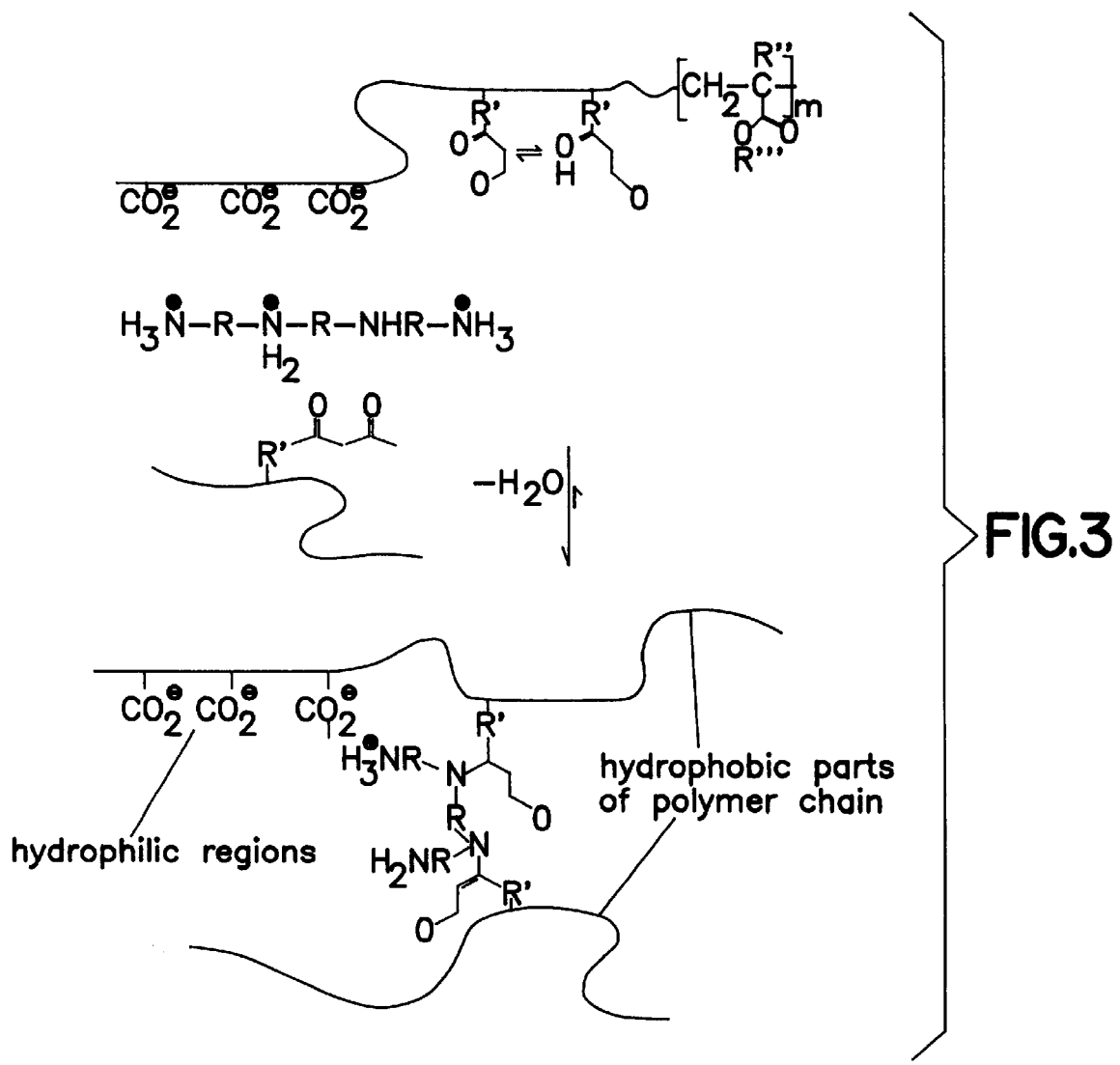

It is certified that error appears in the above-identified patent and that said Letters Patent are hereby corrected as shown below:

In the drawings, replace Figs. 1, 2 and 3 with attached Figs. 1, 2 and 3.

Signed and Sealed this

Eighth Day of February, 2000

*Attest:*

*Attesting Officer*

Q. TODD DICKINSON

*Commissioner of Patents and Trademarks*